US012611300B2

(12) United States Patent
Licht et al.

(10) Patent No.: US 12,611,300 B2
(45) Date of Patent: Apr. 28, 2026

(54) TRANSCATHETER PROSTHETIC ATRIOVENTRICULAR VALVE

(71) Applicant: St. Jude Medical, Cardiology Division, Inc., St. Paul, MN (US)

(72) Inventors: Grayston Licht, Riverside, CA (US); Charles R. Peterson, Murrieta, CA (US); Randolf Von Oepen, Aptos, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 723 days.

(21) Appl. No.: 18/053,917

(22) Filed: Nov. 9, 2022

(65) Prior Publication Data

US 2023/0149157 A1     May 18, 2023

Related U.S. Application Data

(60) Provisional application No. 63/280,673, filed on Nov. 18, 2021.

(51) Int. Cl.
A61F 2/24          (2006.01)
A61B 17/00         (2006.01)
(52) U.S. Cl.
CPC .......... A61F 2/2418 (2013.01); A61F 2/2439 (2013.01); A61F 2220/0025 (2013.01)
(58) Field of Classification Search
None
See application file for complete search history.

(56) References Cited

U.S. PATENT DOCUMENTS

| | | | | |
|---|---|---|---|---|
| 7,530,995 B2 * | 5/2009 | Quijano | ................ | A61F 2/2475 623/1.24 |
| 7,955,374 B2 * | 6/2011 | Erickson | .................... | A61F 2/07 623/1.11 |
| 8,425,593 B2 * | 4/2013 | Braido | .................. | A61F 2/2403 623/2.18 |
| 8,795,354 B2 * | 8/2014 | Benichou | .............. | A61F 2/2412 623/2.11 |
| 8,845,722 B2 * | 9/2014 | Gabbay | ................. | A61F 2/2409 623/2.14 |
| 9,066,801 B2 * | 6/2015 | Kovalsky | .............. | A61F 2/2418 |
| 9,241,792 B2 * | 1/2016 | Benichou | .............. | A61F 2/2433 |

(Continued)

FOREIGN PATENT DOCUMENTS

| | | | | |
|---|---|---|---|---|
| EP | 1849440 A1 * | 10/2007 | ............... | D04C 3/48 |
| EP | 2109417 B1 * | 11/2013 | ............. | A61F 2/966 |

(Continued)

*Primary Examiner* — Ann Hu
(74) *Attorney, Agent, or Firm* — SLEMAN & LUND LLP

(57)          ABSTRACT

A collapsible and expandable prosthetic atrioventricular valve may include an outer stent, an inner stent, and a plurality of prosthetic leaflets mounted within the inner stent. The outer stent may have an atrial disc, a ventricular disc, and a plurality of posts coupling the atrial disc to the ventricular disc. A plurality of connectors may extend between the inner stent and the outer stent to couple the inner stent to the outer stent. The outer stent may be devoid of metal in a space circumferentially extending between adjacent ones of the plurality of posts. The space may extending approximately one half, approximately one third, or approximately one fourth of a circumference of the outer stent.

10 Claims, 18 Drawing Sheets

(56)　　　　References Cited

U.S. PATENT DOCUMENTS

| | | | | |
|---|---|---|---|---|
| 9,572,660 | B2 * | 2/2017 | Braido | A61L 27/54 |
| 9,750,606 | B2 * | 9/2017 | Ganesan | A61F 2/2418 |
| 10,092,400 | B2 | 10/2018 | Jimenez | |
| 10,441,416 | B2 * | 10/2019 | Oba | A61F 2/2418 |
| 11,324,495 | B2 | 5/2022 | Von Oepen | |
| 11,376,119 | B2 | 7/2022 | Quadri | |
| 12,279,948 | B2 * | 4/2025 | Wallace | A61F 2/2418 |
| 12,279,949 | B2 * | 4/2025 | Vidlund | A61F 2/2436 |
| 2005/0075731 | A1 * | 4/2005 | Artof | A61F 2/2439 |
| | | | | 623/2.18 |
| 2005/0177228 | A1 * | 8/2005 | Solem | A61F 2/2451 |
| | | | | 623/2.36 |
| 2006/0122692 | A1 * | 6/2006 | Gilad | A61F 2/2418 |
| | | | | 623/1.35 |
| 2007/0282436 | A1 * | 12/2007 | Pinchuk | A61F 2/2436 |
| | | | | 623/2.11 |
| 2008/0208327 | A1 * | 8/2008 | Rowe | A61F 2/2427 |
| | | | | 604/509 |
| 2009/0248133 | A1 * | 10/2009 | Bloom | A61F 2/91 |
| | | | | 623/1.15 |
| 2010/0016881 | A1 * | 1/2010 | Fleck | A61F 2/0105 |
| | | | | 606/200 |
| 2010/0161036 | A1 * | 6/2010 | Pintor | A61F 2/2433 |
| | | | | 623/2.11 |

| | | | | |
|---|---|---|---|---|
| 2010/0168839 | A1 | 7/2010 | Braido | |
| 2010/0185277 | A1 | 7/2010 | Braido | |
| 2014/0358224 | A1 * | 12/2014 | Tegels | A61L 27/54 |
| | | | | 623/2.14 |
| 2015/0142103 | A1 * | 5/2015 | Vidlund | A61F 2/2439 |
| | | | | 623/2.17 |
| 2016/0228250 | A1 | 8/2016 | Casley | |
| 2016/0317301 | A1 | 11/2016 | Quadri | |
| 2016/0374801 | A1 | 12/2016 | Jimenez | |
| 2017/0056166 | A1 | 3/2017 | Ratz | |
| 2017/0231762 | A1 | 8/2017 | Quadri | |
| 2018/0333259 | A1 | 11/2018 | Dibie | |
| 2019/0192293 | A1 | 6/2019 | Yu | |
| 2020/0030083 | A1 * | 1/2020 | Li | A61F 2/243 |
| 2022/0087814 | A1 | 3/2022 | Vidlund | |
| 2022/0192824 | A1 * | 6/2022 | Vidlund | A61F 2/2409 |
| 2022/0313428 | A1 | 10/2022 | Bergin | |
| 2025/0025295 | A1 * | 1/2025 | Braido | A61F 2/2433 |

FOREIGN PATENT DOCUMENTS

| | | | | | |
|---|---|---|---|---|---|
| WO | WO-03094796 | A1 * | 11/2003 | | A61F 2/2475 |
| WO | WO-2010098857 | A1 * | 9/2010 | | A61F 2/2418 |
| WO | WO-2013059747 | A1 * | 4/2013 | | A61F 2/2418 |
| WO | WO-2013116785 | A1 * | 8/2013 | | A61F 2/2436 |
| WO | WO-2019205644 | A1 * | 10/2019 | | A61F 2/2418 |

* cited by examiner

320

320a

320b

322

1100a 1170a          1190a          1190a

1170a 1100b     1170b          1190b                    1190b
                1170b

TRANSCATHETER PROSTHETIC ATRIOVENTRICULAR VALVE

CROSS-REFERENCE TO RELATED APPLICATIONS

This application claims priority to the filing date of U.S. Provisional Patent Application No. 63/280,673, filed Nov. 18, 2021, the disclosure of which is hereby incorporated by reference herein.

BACKGROUND OF THE DISCLOSURE

The heart has four native valves, including the aortic valve, the pulmonary valve, the mitral valve (also known as the left atrioventricular valve), and the tricuspid valve (also known as the right atrioventricular valve). When these valves begin to fail, for example by not fully coapting and allowing retrograde blood flow (or regurgitation) across the valve, it may be desirable to repair or replace the valve. Prosthetic replacement heart valves may be surgically implanted via an open-chest, open-heart procedure while the patient is on cardiopulmonary bypass. However, such procedures are extremely invasive and frail patients, who may be the most likely to need a prosthetic heart valve, may not be likely to survive such a procedure. More recently, prosthetic heart valves have been trending to less invasive procedures, including collapsible and expandable heart valves that can be delivered through the vasculature in a transcatheter procedure.

The aortic valve and the pulmonary valve typically have a relatively circular shape and a relatively small diameter compared to the left and right atrioventricular valves. As a result, transcatheter prosthetic heart valves designed for the mitral and tricuspid valve may have significantly larger challenges that need to be overcome compared to transcatheter prosthetic heart valve designs for the aortic and pulmonary valves.

Another challenge in designing transcatheter prosthetic atrioventricular valves is avoiding or limiting conduction disturbances. When a transcatheter prosthetic atrioventricular valve is expanded into the native mitral or tricuspid valve, the device may press against tissue and result in disturbances of the natural conduction system of the heart. Because of this, pacemakers are frequently implanted along with prosthetic atrioventricular valves in order to help override any such conduction disturbances.

Another challenge in designing transcatheter prosthetic atrioventricular valves is allowing for the prosthetic valve to be recaptured (e.g., re-collapsed into a delivery device) after it has been at least partially expanded. Due to the typical size of a prosthetic atrioventricular valve being relatively large, as well as the potential inclusion of both an outer anchoring frame and an inner valve frame, the forces involved in recapturing a prosthetic atrioventricular valve may be relatively large, rendering such recapture relatively difficult.

BRIEF SUMMARY OF THE DISCLOSURE

This disclosure is generally directed to collapsible and expandable prosthetic atrioventricular valves that may limit conduction disturbances while providing for effective fixation. These valves may be best suited for replacing native mitral valves, and particularly native tricuspid valves. These prosthetic transcatheter atrioventricular valves may be generally include a collapsible and expandable stent, a collapsible and expandable valve assembly coupled to the stent.

The stent may include an outer stent, generally meant to achieve fixation within the native valve annulus, and an inner stent, generally meant to provide a support for bioprosthetic leaflets of the valve assembly. The inner stent may be generally cylindrical and may be attached to the outer stent in a way which allows the bioprosthetic valve assembly to maintain a generally cylindrical shape, even when forces applied to the outer stent distort the shape of the outer stent. The valve assembly may include a plurality of bioprosthetic leaflets (typically three leaflets, although two leaflets or more than three leaflets may be provided). The valve assembly may include one or more skirts or cuffs on inner and/or outer surfaces of the inner and/or outer stent to help provide a seal between the inside of the native valve annulus and the outside of the bioprosthetic leaflets.

According to one aspect of the disclosure, a collapsible and expandable prosthetic atrioventricular valve includes an outer stent having an atrial disc, a ventricular disc, and a plurality of posts coupling the atrial disc to the ventricular disc, and an inner stent. A plurality of connectors may extend between the inner stent and the outer stent to couple the inner stent to the outer stent. A plurality of prosthetic leaflets may be mounted within the inner stent. The outer stent may be devoid of metal in a space circumferentially extending between adjacent ones of the plurality of posts, the space extending approximately one-third of a circumference of the outer stent. The atrial disc may have two circumferential rows of cells, and the ventricular disc may have one circumferential row of cells. The atrial disc may have one circumferential row of cells, and the ventricular disc may have two circumferential rows of cells. The plurality of posts may includes three posts, each of the three posts including two struts extending from the atrial disc to the ventricular disc. The two struts of each of the three posts may have a first end coupled to a respective first apex of a cell in the atrial disc, and a second end coupled to a respective second apex of a cell in the ventricular disc. Each of the three posts may include a tine between the two struts. An aperture may be formed in one of the two struts or the tine of each of the three posts, each of the plurality of connectors being coupled to the outer stent via a corresponding one of the apertures. In an expanded condition of the prosthetic atrioventricular valve, a diameter of the outer stent at the plurality of posts may be smaller than diameters of the outer stent at the atrial disc and the ventricular disc. The inner stent may include a circumferential row of first cells having a total number, and the outer stent may include a circumferential row of second cells having a total number, the total number of second cells being a whole number multiple of the total number of first cells. The total number of second cells may be twenty-seven, and the total number of first cells may be nine.

According to a second aspect of the disclosure, a method of replacing a native atrioventricular valve of a heart may include delivering a prosthetic atrioventricular valve to the native atrioventricular valve while the prosthetic atrioventricular valve is collapsed within a delivery catheter, the prosthetic atrioventricular valve including an outer stent, an inner stent coupled to the outer stent, and a plurality of prosthetic leaflets mounted within the inner stent. The prosthetic atrioventricular valve may be deployed from the delivery catheter to allow the prosthetic atrioventricular valve to self-expand. Allowing the prosthetic atrioventricular valve to self-expand may include positioning an atrial disc of the outer stent on an atrial side of the native atrioventricular valve and positioning a ventricular disc of the outer stent on a ventricular side of the native atrioventricular valve. After the prosthetic atrioventricular valve has self-expanded into the native atrioventricular valve, a gap in the outer stent between an adjacent pair of posts that connect that atrial disc to the ventricular disc may be aligned with a conduction system of the heart.

According to a third aspect of the disclosure, a prosthetic atrioventricular valve system may include an outer stent having an atrial portion and a ventricular portion, an inner stent, a plurality of connectors extending between the inner stent and the outer stent to couple the inner stent to the outer stent, and a plurality of prosthetic leaflets mounted within the inner stent. The outer stent may include one or more circumferential rows of cells and a plurality of rails extending in an axial direction from the atrial portion to the ventricular portion. The cells of the one or more circumferential rows of cells of the outer stent may be diamond-shaped. Each of the plurality of rails may include a connector at a terminal end thereof. At least one flexible control member may be coupled to the connector of each of the plurality of rails. The flexible control member may be a suture. In a retrieval condition of the prosthetic atrioventricular valve system, the outer stent may be at least partially deployed from a delivery catheter, and the flexible control member may extend proximally through an interior of the delivery catheter.

According to a fourth aspect of the disclosure, a method of recapturing a prosthetic atrioventricular valve may include delivering the prosthetic atrioventricular valve to a native atrioventricular valve while the prosthetic atrioventricular valve is collapsed within a delivery catheter, the prosthetic atrioventricular valve including an outer stent having an atrial portion and a ventricular portion, an inner stent coupled to the outer stent, and a plurality of prosthetic leaflets mounted within the inner stent, the outer stent including one or more circumferential rows of cells and a plurality of rails extending in an axial direction from the atrial portion to the ventricular portion. The prosthetic atrioventricular valve may be deployed from the delivery catheter to allow the prosthetic atrioventricular valve to at least partially self-expand. After allowing the prosthetic atrioventricular valve to at least partially self-expand, the prosthetic atrioventricular valve may be retrieved into a retrieval catheter. Retrieving the prosthetic atrioventricular valve may include causing the prosthetic atrioventricular valve to collapse into the retrieval catheter by manipulating at least one flexible control member coupled to a plurality of connectors, each of the plurality of connectors coupled to a corresponding one of the plurality of rails. The retrieval catheter may be the delivery catheter. The retrieval catheter may be a separate device from the delivery catheter, and after deploying the prosthetic atrioventricular valve from the delivery catheter, and before retrieving the prosthetic atrioventricular valve, the retrieval catheter may be advanced along or through delivery catheter.

DETAILED DESCRIPTION OF THE DISCLOSURE

Figure 1:
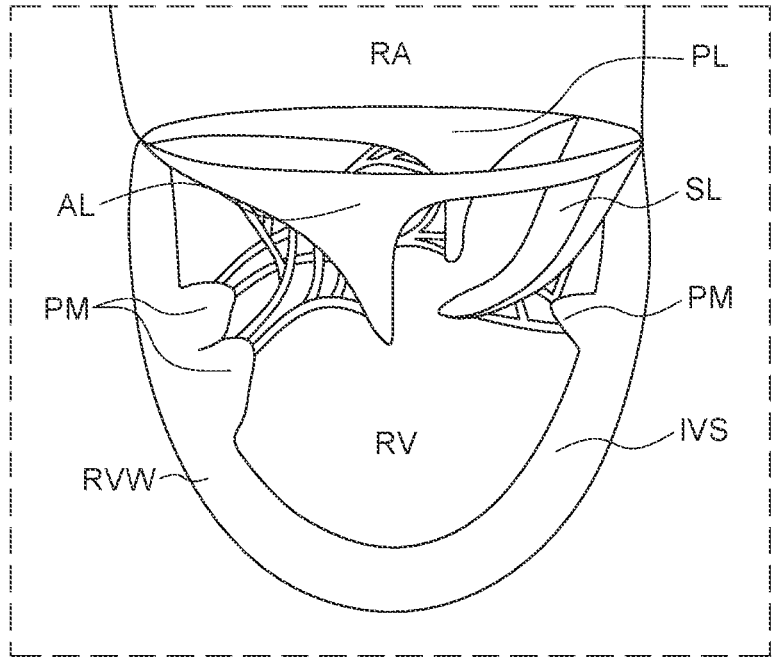
FIG. 1 is a schematic illustration of the right atrioventricular valve.

FIG. 1 is a schematic illustration of the right atrioventricular valve (commonly referred to as the tricuspid valve). The tricuspid valve separates the right atrium RA from the right ventricle RV and typically has three leaflets, including a posterior leaflet PL, an anterior leaflet AL, and a septal leaflet SL. The septal leaflet SL is positioned nearest the interventricular septum IVS. The tricuspid valve annulus may include conduction nodes near the connection point between the annulus and the septal leaflet, including for example the atrioventricular ("AV") node. Electrical impulses may be conducted from the AV node, via the bundle of His, to the Purkinje fibers that provide electrical conduction to the ventricles. Papillary muscles PM along the right ventricular wall RVW may support chordae tendineae coupled to the tricuspid valve leaflets to prevent inversion of the leaflets during normal physiological operation. The left atrioventricular valve (commonly referred to as the mitral valve) may have a generally similar structure as the tricuspid valve, although many differences do exist—including for example mitral valve typically includes two leaflets (an anterior and posterior leaflet) and has the general shape of a hyperbolic paraboloid or "saddle"-type shape. Both the mitral valve annulus and tricuspid valve annulus may be very large compared to the aortic and pulmonary valves. For example, the tricuspid valve may have a diameter of between 45-50 mm in a patient with moderate tricuspid valve disease, and a diameter of between 50-60 mm in a patient with severe tricuspid valve disease. Depending on the stage of tricuspid regurgitation, the tricuspid valve annulus may have an enlarged diameter of up to 70 mm.

Figure 2:
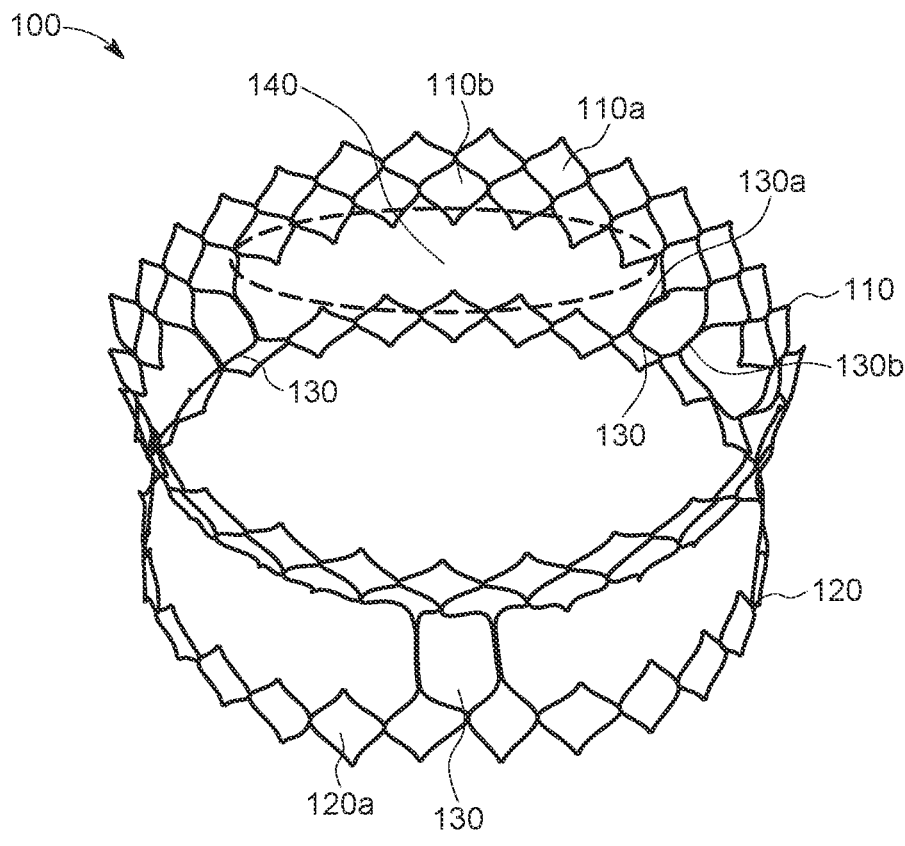
FIG. 2 is a side perspective view of an outer stent of a prosthetic atrioventricular valve according to one aspect of the disclosure.

FIG. 2 is a side perspective view of an outer stent 100 of a prosthetic atrioventricular valve according to one aspect of the disclosure. FIG. 2 shows the outer stent 100 in isolation from the rest of the prosthetic heart valve and omits structures such as an inner stent and prosthetic leaflets carried by the inner stent, and one or more sealing cuff and/or skirts on the inner and/or outer surfaces of the inner and/or outer stent. The outer stent 100 of FIG. 2 is collapsible and expandable and may be formed of a shape memory metal such as nitinol. The outer stent 100 of FIG. 2 may be generally circular (and/or rotationally symmetric) when in the illustrated expanded condition. The outer stent 100 may include one or more rows of cells (e.g., diamond-shaped cells) in an atrial disc section 110 (which may also be referred to as an atrial flare or atrial anchor section), and one or more rows of cells (e.g. diamond-shaped cells) in a ventricular section 120 (which may also be referred to as a ventricular flare or ventricular anchor section). In the illustrated embodiment, the atrial section 110 includes two rows of diamond-shaped cells, including a first row of cells 110*a* and a second row of cells 110*b* positioned downstream (in an outflow direction) of the first row of cells 110*a*. In the illustrated embodiment, the ventricular section 120 includes a single row of diamond-shaped cells 120*a*. However, in other embodiments, the atrial section 110 may include more or fewer rows of cells, the ventricular section 120 may include more than one row of cells, and the cells may form shapes other than diamond shapes.

The atrial section 110 may be coupled to the ventricular section 120 only at selected locations around the circumference of the outer stent 100, with a large amount of space 140 remaining devoid of metal stent structure circumferentially between those connection points. In FIG. 2, the connection points include three double clips 130. As shown, the double clips 130 are positioned at equidistant locations around the circumference of the outer stent 100, but in other embodiments the positioning may be other than equidistant. Each double clip 130 may include a first generally axial stent post 130*a* extending from a top apex of a first ventricular stent cell 120*a* to a bottom apex of a first atrial stent cell in the second row 110*b*, and a second generally axial stent post 130*b* extending from a top apex of a second ventricular stent cell 120*a* to a bottom apex of a second atrial stent cell in the second row 110*b*. The first atrial stent cell may be directly adjacent to the second atrial stent cell, and the first ventricular stent cell may be directly adjacent to the second ventricular stent cell. If three double clips 130 are provided, the space 140 devoid of metal stent structure extends approximately one-third the circumference of the outer stent 100 (but slightly less due to the size of the double clips 130). If two double clips 130 were provided, the space 140 devoid of metal stent material would be approximately half the circumference of the outer stent 100. If four double clips 130 were provided, the space 140 devoid of metal stent material would be approximately one-fourth the circumference of the outer stent 100, etc.

In the embodiment illustrated in FIG. 2, the atrial disc 110 includes two rows 110*a*, 110*b* of stent cells, with 27 cells each, and the ventricular disc 120 includes one row of stent cells 120*a* with 27 cells. However, as noted above, more or fewer rows may be provided in the atrial section 110, and more rows may be provided in the ventricular section 120. Fewer rows in the ventricular section 120 may be desirable in some embodiments to minimize the amount of structure extending into the right (or left) ventricle, and thus minimize the amount of structure available to block the right ventricular outflow tract ("RVOT") (or the left ventricular outflow tract ("LVOT")). In some embodiments, it may be desirable to include a number of cells in each row 110*a*, 110*b*, 120*a* that is a multiple of three or a multiple of nine, particularly if the inner stent (which may be similar or the same as any of the inner stents described below) includes rows of 3 or 9 cells (or multiples thereof), as such correspondence may maximize the ability to provide regular positioning of members that couple the inner stent to the outer stent 100. However, it should be understood that more or fewer than 27 cells may be provided in each row 110*a*, 110*b*, 120*a*. Also, if the inner stent includes a number of cells per row that is different than 9, it may be desirable for each row of cells 110*a*, 110*b*, 120*a* in the outer stent 100 to include a multiple (e.g., an integer or whole number multiple) of that different number. However, in still other embodiments, such correspondence between the numbers of cells in each row of the inner stent to the number of cells in the rows of the outer stent 100 need not be provided.

The connectors between the atrial disc 110 and ventricular disc 120 may be utilized as anchor points to couple the inner stent to the outer stent 100. For example, in FIG. 2, a total of three or six connection points may be utilized to couple the inner stent to the outer stent 100, since there are three double clips 130.

As shown in FIG. 2, there is no metal stent structure positioned axially between the ventricular disc 120 and the atrial disc 110 in the circumferential direction between circumferentially adjacent double clips 130. The atrioventricular valve pseudo-annulus may generally align with this void space 140 (and with the double clips 130), when the prosthetic valve is implanted. This large void space 140 reduces the contact between the outer stent 100 and the native valve annulus, particularly reducing metal-to-tissue contact in these areas. Preferably, when implanted, the void space 140 is aligned with the base of the septal leaflet SL (if implanting into the tricuspid valve) to reduce or eliminate contact with the AV node, thus minimizing or eliminating the likelihood of conduction disturbances. The same or similar positioning may be used if implanting the prosthetic valve into the native mitral valve annulus to avoid conduction disturbances. In some patients, a pacemaker may already be implanted into the heart, or it may nonetheless be desirable to implant a pacemaker despite the reduced disturbance to the conduction system. The conduction gaps 140 in the outer stent 100 may, in those circumstances, additionally help to avoid interfering with any pacemaker leads near the prosthetic heart valve.

When implanted, the outer stent 100 of FIG. 2 may provide suitable fixation despite the voids 140 provided in the outer stent. For example, the outflow end of the atrial disc 110 may "bite into" the native annulus upon deployment, and the inflow end of the ventricular disc 120 may "bite into" the native leaflets, in order to provide good engagement with the native tissue. For example, the outflow apices of the second row 110*b* of atrial cells and the inflow apices of the first row 120*a* of ventricular cells may engage with native tissue. It should be understood that expansion forces of the outer stent 100 may also provide an amount of fixation within the native valve. Because the prosthetic valves described herein are intended for transcatheter implantation, these prosthetic valves would typically not be sutured to the native annulus, and thus must maintain sufficient fixation without sutures or similar fixation mechanisms typically used in surgical valve implantations. The connectors between the atrial disc 110 and the ventricular disc 120 (e.g., the three double clips 130 shown in FIG. 2) will also push against the native annulus to assist with fixation. Although not shown, the outer stent 100 shown in FIG. 2 may include a skirt or cuff (e.g., a synthetic fabric like PET or PTFE) to provide sealing between the outer stent 100 and the native valve annulus. The skirt or cuff may extend over the entire outer stent 100, including in the spaces 140 that are void of metal structure. The existence of the skirt or cuff in this area is not expected to cause any significant conduction disturbances, even when aligned with the AV node, at least because the material is a generally soft, non-metallic material.

Also, although not shown in FIG. 2, other anchoring features may be provided to help maintain engagement of the prosthetic heart valve within the native valve annulus once deployed. For example, needles, hooks, barbs, paddles, tines, etc. may be provided on the outer stent 100, with those features engaging native tissue to provide even further fixation.

In some circumstances, the areas 140 of the outer stent 100 that are void of metal may create potential issues when loading the prosthetic heart valve into a catheter for delivery, or when deploying the prosthetic heart valve from the catheter. This discontinuity in metal structure may tend to cause the ventricular disc 120 to "want" to invert upon deployment (as it is the first section that is released from the catheter during transseptal delivery), or upon loading into the catheter for insertion into the patient. The inflow apices of the ventricular cells 120a may also tend to result in the ventricular disc 120 biting into, or otherwise not smoothly loading into, the delivery catheter upon loading of the prosthetic heart valve into the delivery catheter. For example, as the prosthetic heart valve is collapsed and drawn into the catheter (e.g., via a funnel), the inflow apices of the ventricular stent cells 120a may tend to hook over or bite into structures of the loading funnel and/or the catheter during loading. In order to minimize the likelihood of one or more of the above issues occurring, additional fixation structures may be provided to couple the atrial disc 110 to the ventricular disc 120. For example, one or more suture lines may be provided to couple the inflow apex of one or more ventricular cells 120a to the outflow apex of one or more atrial cells in the second row 110b. Such fixation structures may extend longitudinally or diagonally, and any number may be provided. Such fixation structures may tend to allow for a smoother deployment and loading of the prosthetic heart valve, despite the areas 140 devoid of metal between the ventricular disc 120 and atrial disc 110. However, as noted above, these fixation structures are preferably soft and/or non-metal, so that such structures do not create any conduction disturbances that might otherwise occur if metal structure was pressing into native annulus at or near the AV node. It should further be understood that, if these fixation structures are provided, they would preferably only be provided where the stent cells are "free-floating"—e.g., not in the areas where the double clips 130 are provided.

Figure 3:
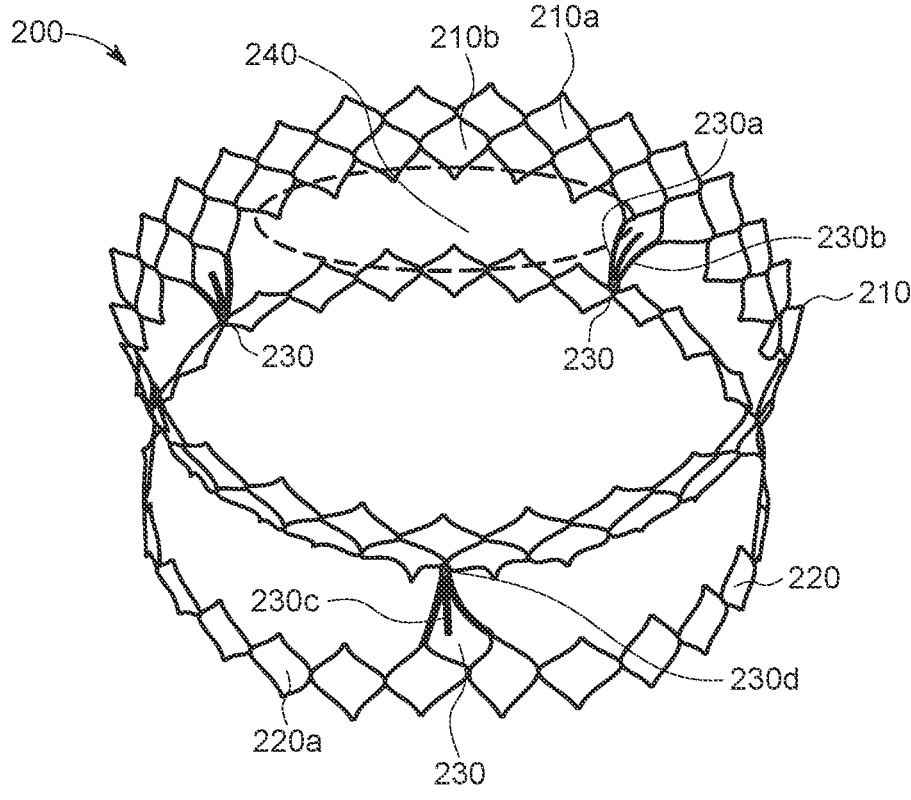
FIG. 3 is a side perspective view of an outer stent of a prosthetic atrioventricular valve according to another aspect of the disclosure.

FIG. 3 is a side perspective view of an outer stent 200 of a prosthetic atrioventricular valve according to another aspect of the disclosure. The outer stent 200 of FIG. 3 is identical to the outer stent 100 of FIG. 2 in most respects, and thus for brevity, only the differences will be described. Reference numbers for stent 200 used in FIG. 3 that refer to similar or identical components in stent 100 are increased by 100 (e.g., atrial rows 210a, 210b correspond to atrial rows 110a, 110b, respectively). Whereas the outer stent 100 of FIG. 2 is shown with three double clips 130 that couple the atrial disc 110 to the ventricular disc 120, the outer stent 200 of FIG. 3 is shown with similar double clips 230 with an additional tine 230c in between the double clips or posts 230a, 230b. These additional tines 230c may provide for additional anchoring by pressing against and/or engaging native tissue for fixation during deployment of the outer stent 200 into a native valve annulus. Also shown in FIG. 3 at the clips/posts 230 (e.g., near a base of tines 230c) is an aperture 230d that may be utilized for coupling a coupling member, with the other ends of the coupling members attaching to the inner stent, as shown in other figures below.

Figure 4:
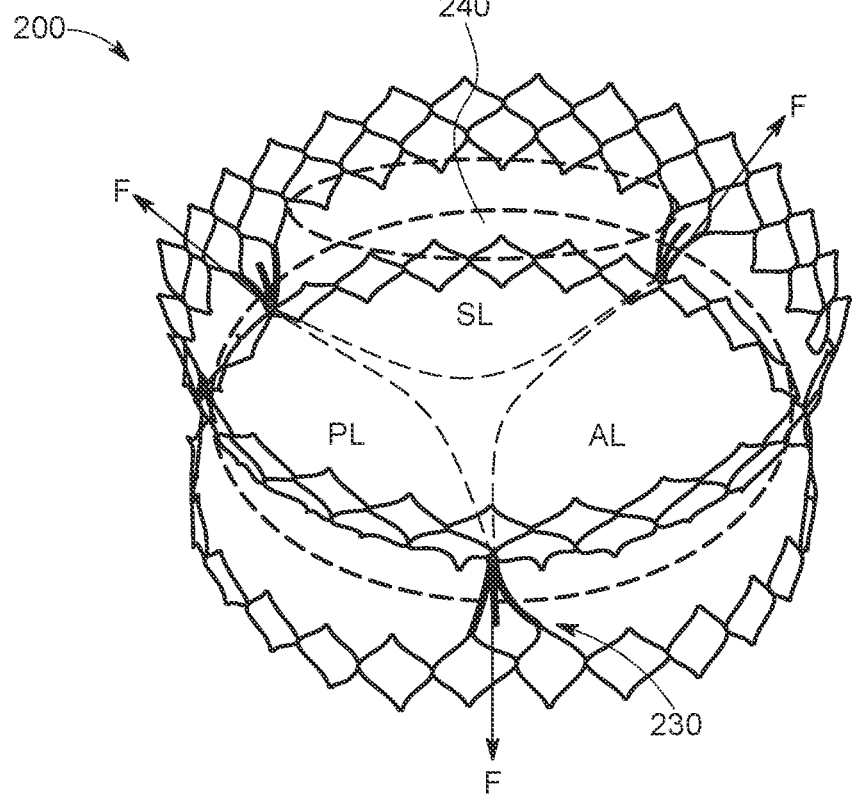
FIG. 4 shows the outer stent of FIG. 3, with annotations illustrating relative positioning of structures of a native tricuspid valve following implantation.

FIG. 4 shows the outer stent of FIG. 3, with annotations illustrating relative positioning of structures of a native tricuspid valve, including the anterior leaflet AL, septal leaflet SL, and posterior leaflet PL, following implantation. As shown, in one implanted condition, the clips/posts 230 generally align with the native commissures, and one of the conduction gaps 240 aligns with the base of the septal leaflet SL where the AV node is expected to be located. In other words, the forces F of the outer stent 200 pressing on the native valve annulus are mostly concentrated at the clips/posts 230, with little or no force F being applied directly to the base of the septal leaflet SL, minimizing or eliminating the likelihood of conduction disturbances.

Figure 5:
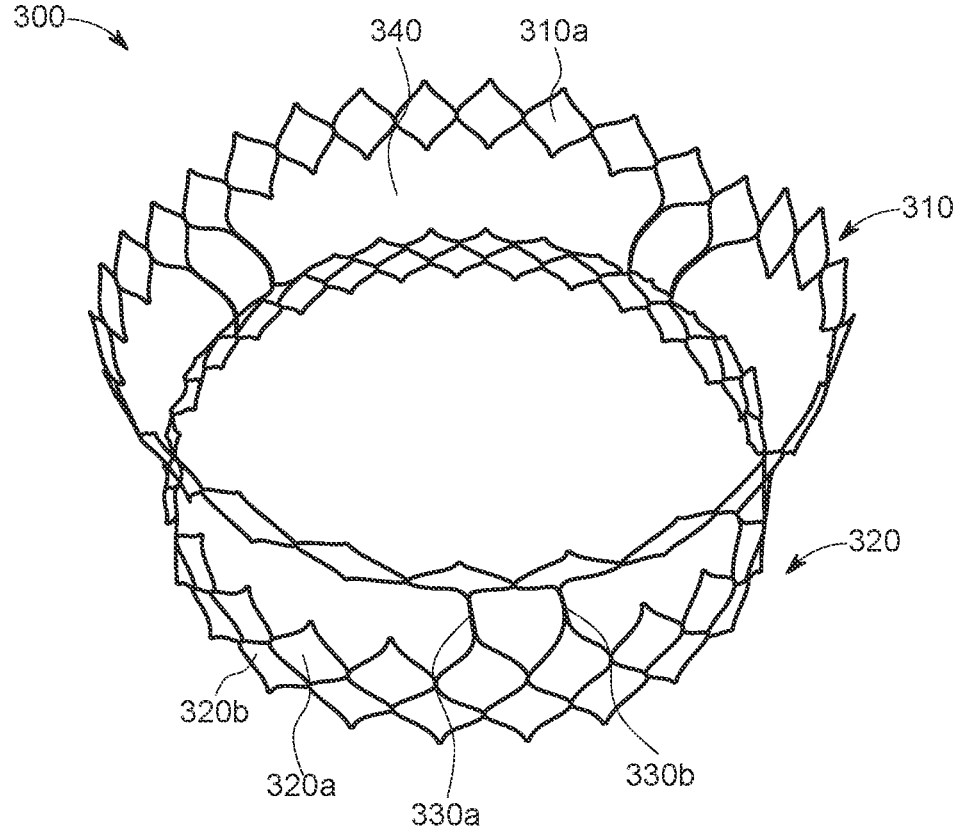
FIG. 5 shows a side perspective view of an outer stent of a prosthetic atrioventricular valve according to a further aspect of the disclosure.
Figure 6:
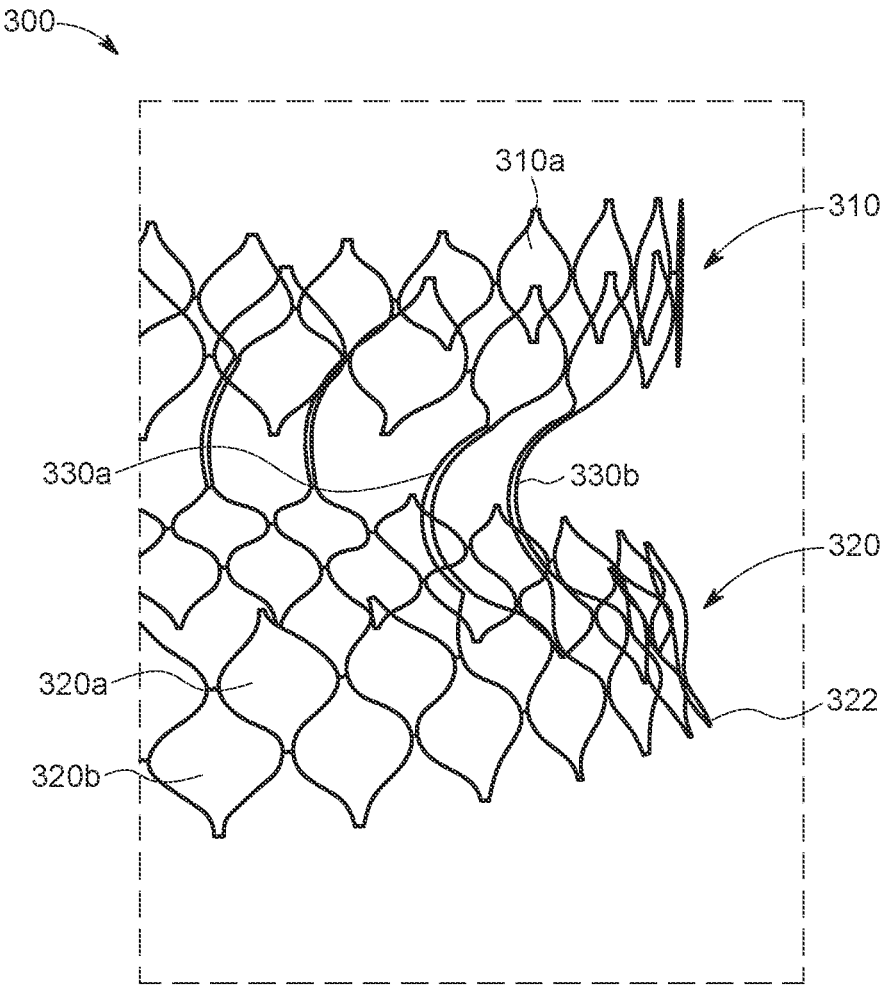
FIG. 6 shows a side view of the outer stent of FIG. 5.
Figure 7:
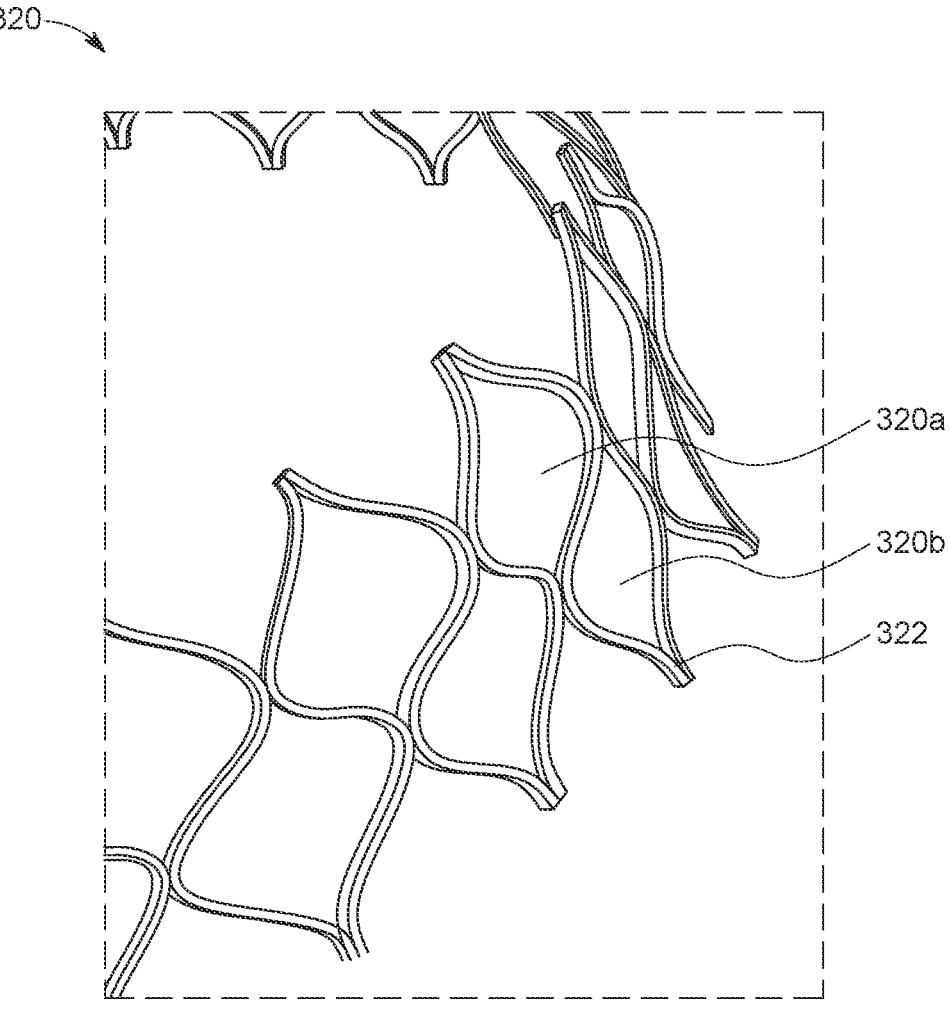
FIG. 7 shows an enlarged view of the ventricular disc of the outer stent of FIG. 5.

FIG. 5 shows a perspective view of an outer frame 300 according to a further aspect of the disclosure. FIG. 6 shows a partial side view of the outer stent 300 of FIG. 5. FIG. 7 shows an enlarged view of the ventricular disc 320 of the outer stent 300 of FIG. 5. The outer stent 300 of FIGS. 5-7 is generally similar to that shown in FIG. 2, with certain differences. For the purpose of brevity, only the differences are described here. Reference numbers for outer stent 300 used in FIGS. 5-7 that refer to similar or identical components in stent 100 are increased by 200 (e.g., atrial disc 310 and ventricular disc 320 correspond to atrial disc 110 and ventricular disc 120 respectively). One difference is that, instead of including two rows of cells 110a, 110b at the atrial disc 110 and one row of cells 120a at the ventricular disc 120, the outer stent 300 of FIGS. 5-7 includes one row of cells 310a at the atrial disc 310 and two rows of cells 320a, 320b at the ventricular disc. As best shown in FIGS. 6-7, the ventricular disc 320 may include an outward flare 322, particularly at the outflow end of the ventricular disc 320, including at the outflow end of the outflow row of cells 320b. This outward flare 322 may help better engage tissue on the ventricular side of the valve annulus, such as tissue of the native leaflets. The inclusion of two rows of cells 320a, 320b at the ventricular disc 320 may provide additional surface area for anchoring or fixing the outer stent 300 within the native valve annulus. As best shown in FIG. 6, the posts 330a, 330b coupling the atrial disc 310 to the ventricular 320 disc may have a "C" or "U"-shape in the expanded condition, with the "C" or "U"-shape configured to receive portions of the native valve annulus therein to better anchor the prosthetic heart valve within the native valve annulus. In other words, the posts 330a, 330b may define a diameter that is smaller than the diameters of both the atrial and ventricular discs in the expanded condition of the outer frame 300 (and in the expanded condition of the prosthetic heart valve that incorporates the outer frame 300).

Figure 8:
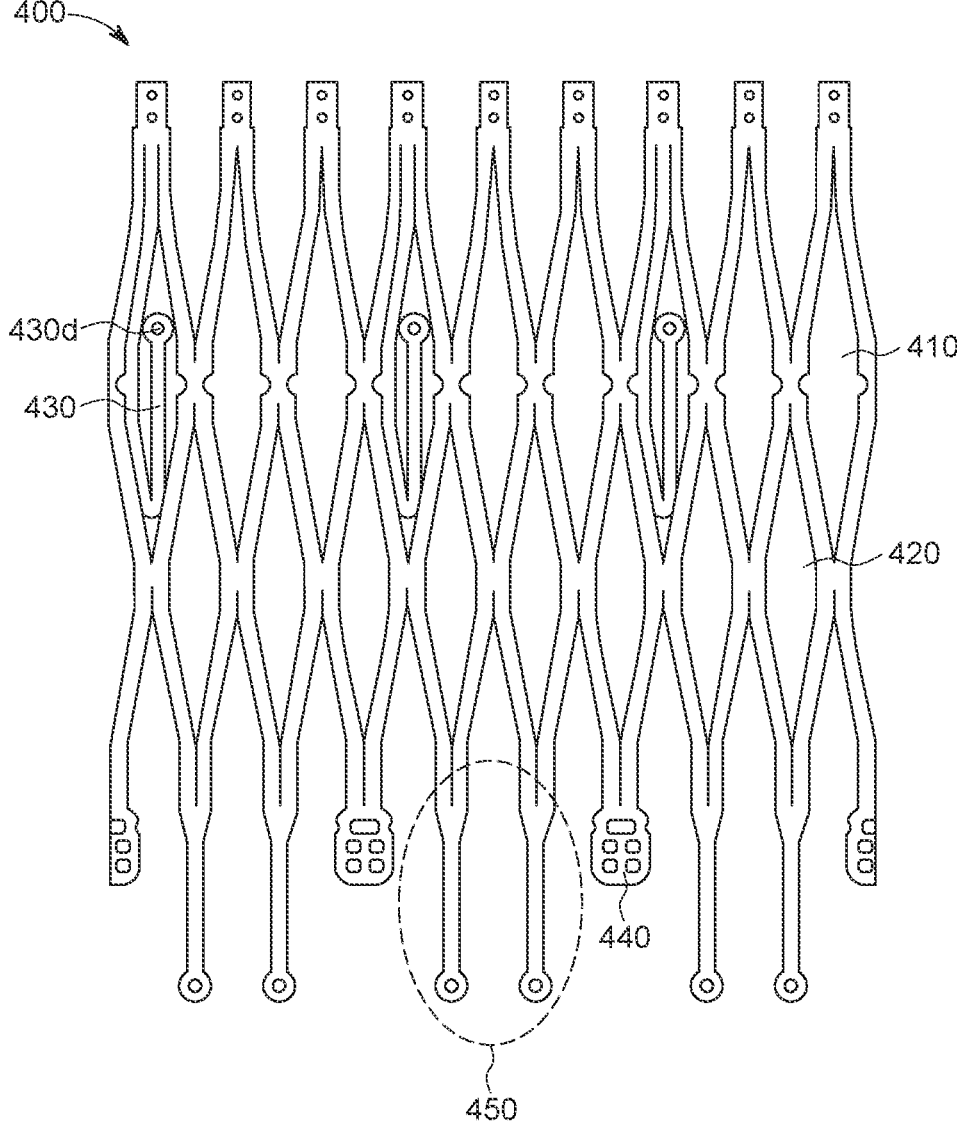
FIG. 8 is a developed view of an inner stent according to an aspect of the disclosure.

FIG. 8 is a developed view of an inner frame or stent 400 according to an aspect of the disclosure as if cut longitudinally and laid flat on a table. In an expanded or deployed condition, the inner stent 400 may be generally cylindrical and be positioned radially inside the outer stent (e.g., outer stents 100, 200, 300 or other outer stents). As with the outer stent, the inner stent 400 may be formed from a collapsible and expandable material, such as a shape memory metal, including nitinol. In the illustrated embodiment, the inner stent 400 includes two rows of generally diamond-shaped cells, including a top inflow row 410 and a bottom outflow row 420, with nine cells in each row. However, as noted above, the inner stent 400 may include more or fewer cells in each row 410, 420, and in some embodiments may include more or fewer rows of cells. A plurality of connectors 430 may be provided with the inner stent 400. In the illustrated embodiment, three connectors 430 are provided within every third cell in the inflow row 410, although more or fewer connectors 430 may be provided. Preferably, the number of connectors 430 is the same as the number of posts or other connecting features that couple the atrial disc of the outer stent to the ventricular disc of the outer stent. In the expanded condition of the inner stent 400, each connector 430 may extend radially outwardly and couple to the outer stent at the outer stent posts. In the illustrated embodiment, each connector 430 includes an aperture 430*d* near a terminal end thereof, and each post of the outer stent may include a corresponding aperture (e.g., aperture 230*d* of double clips 230 of outer stent 200), with rivets, sutures, or other fasteners coupling the inner stent connectors 430 to the outer stent posts via the apertures. However, it should be understood that other fastening modalities may be appropriate. In the illustrated embodiment of the inner stent 400, the connectors 430 are formed of the same material as the inner stent 400 and may be integral therewith. The connectors 430 may be formed, for example, by laser cutting a tube of nitinol to create the inner stent 400 shown in FIG. 8. The inner stent may include commissure attachment features 440, illustrated as generally rectangular or square stent features at the outflow end of every third cell in the ventricular row 420. The commissure attachment features ("CAFs") 440 may include apertures and may be used to couple (for example via sutures) two adjacent bioprosthetic leaflets to the inner stent 400 at the CAFs 440. Three CAFs 440 are shown in FIG. 8 because the prosthetic heart valve incorporating the inner stent 400 of FIG. 8 includes three prosthetic (e.g., bioprosthetic or synthetic) leaflets. Some or all of the ventricular cells 420 that do not have CAFs 440 may include stent extensions 450 that may extend radially outwardly when expanded and attach to the ventricular disc of the outer stent in order to help stabilize the ventricular disc of the outer stent when the prosthetic heart valve is implanted. The length of the stent extensions 450 of the inner frame 400 could be increased and, instead of coupling to the outer frame, engage with native anatomical structures, such as native leaflets or chordae tendineae, to help further secure the prosthetic heart valve in place. In other embodiments, the outer stent may instead or additionally include stent extensions similar to those shown for the inner stent in FIG. 8.

Figure 9:
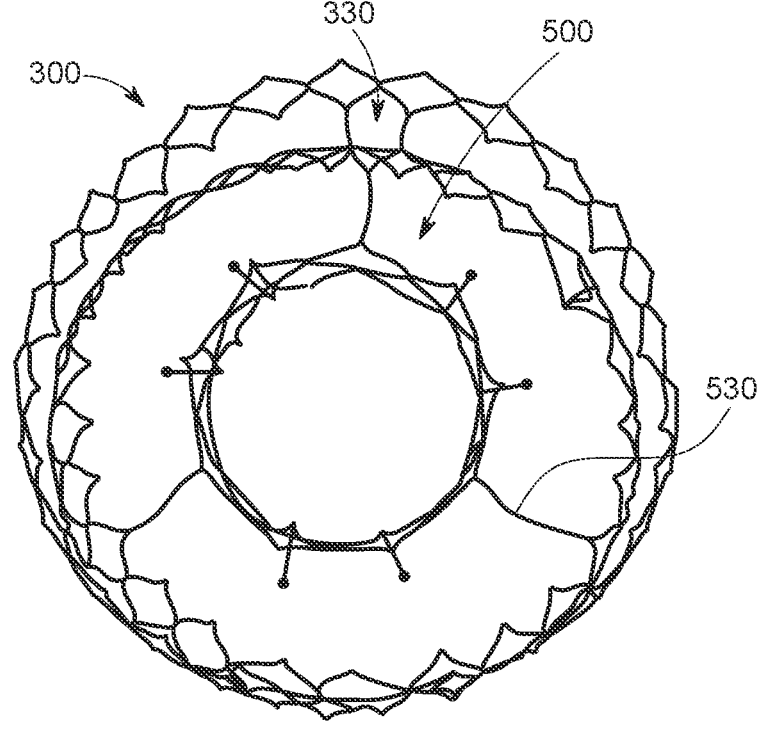
FIG. 9 is a top-down view of the outer stent of FIG. 5 coupled with an inner stent similar to that shown in FIG. 8.
Figure 10:
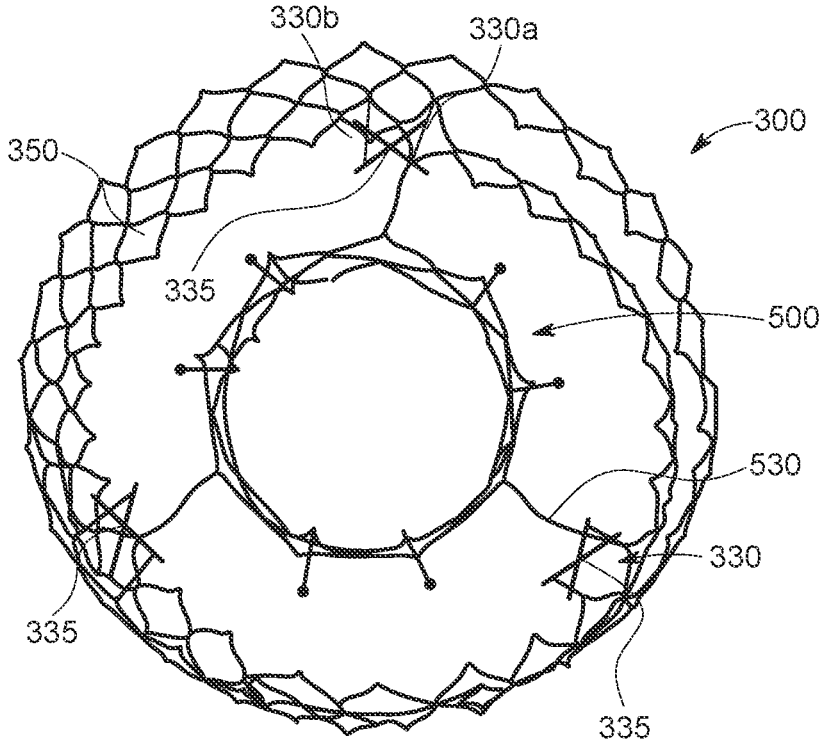
FIG. 10 shows the configuration of FIG. 9 with additional features provided.

FIG. 9 illustrates a top-down view of the outer stent 300 of FIG. 5 coupled to an inner stent 500 similar to that shown in FIG. 8. The only difference between inner stent 500 and inner stent 400 is that inner stent 500 omits the stent extensions 450 that are part of inner stent 400. Notably, the three connectors 530 of the inner stent 500 extend outwardly from the inner stent 500 and couple to an individual post 330*a* or 330*b* of each double clip 330. However, in other embodiments, the three connectors 530 of the inner stent 500 could separate, branch, or split near a terminal end thereof so that each of the three connectors 530 of the inner stent 500 could attach to each post 330*a*, 330*b* of each double clip 330. In this particular embodiment, it should be understood that there is rotational symmetry of the inner stent 500 and the outer stent 300, allowed at least in part by including nine cells in each row of the inner frame 500 and a multiple of nine cells (27 in this embodiment) in each row of the outer frame 300. FIG. 10 shows the same configuration as shown in FIG. 9, with certain additional features shown. In particular, FIG. 10 illustrates that either post 330*a* or 330*b* of each clip 330 (if only one post is being used) of the outer stent 300 may serve as an attachment site 335 of the inner stent connectors 530. FIG. 10 also shows that, as noted above, a skirt or cuff and/or suture materials 350 may be provided between the atrial disc 310 and the ventricular disc 320 of the outer frame 300, spanning the areas 340 void of metal between the atrial disc 310 and the ventricular disc 320. And although FIG. 10 only shows a single void area 340 covered by skirt and/or cuff and/or suture materials, it should be understood that all of the void areas 340 may be covered by skirt and/or cuff and/or suture materials. Although embodiments herein are generally disclosed and/or shown with rows of cells having nine cells, or a whole-number multiple of nine cells, it should be understood that other numbers (and whole-number multiples) may be suitable. For example, particularly when the inner stent (e.g., 400 or 500) includes a set of three prosthetic leaflets mounted therein, the inner stent preferably includes a total number of cells that is a whole-number multiple of three (e.g., 3, 6, 9, 12, 14, 18, 21, etc.). In such an embodiment, it may also be preferable for the outer stent to have rows of cells having a number of cells that are a whole-number multiple of three, and particularly a whole-number multiple of the number of cells in the rows in the inner stent.

Figure 11:
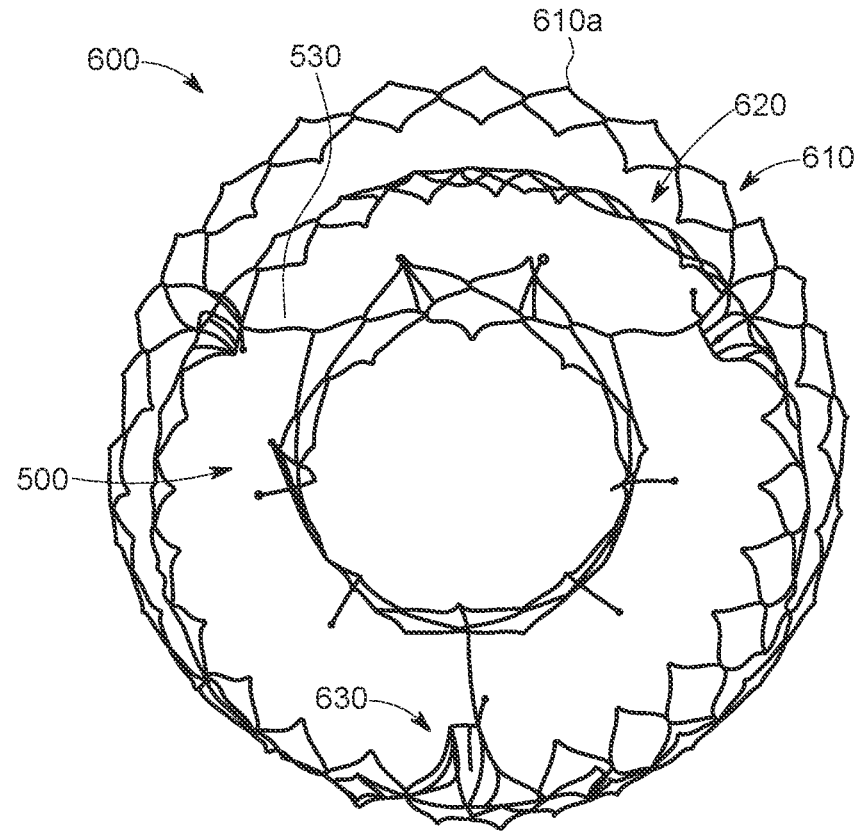
FIG. 11 is a top-down view of an outer stent similar to FIG. 5 coupled with the inner stent of FIG. 8.

FIG. 11 illustrates a top-down view of an outer stent 600 that is similar to outer stent 300 of FIG. 5, in that the atrial disc 610 includes one row of cells 610*a* and the ventricular disc 620 includes two rows of cells with the same configuration as outer stent 300, but having double clips 630 that are substantially similar or identical to double clips 230 of outer stent 200. FIG. 11 shows outer stent 600 coupled to inner stent 500. As can be seen, the three inner stent connectors 530 extend radially outward to couple to the clips or posts 630 of the outer stent 600.

Figure 12:
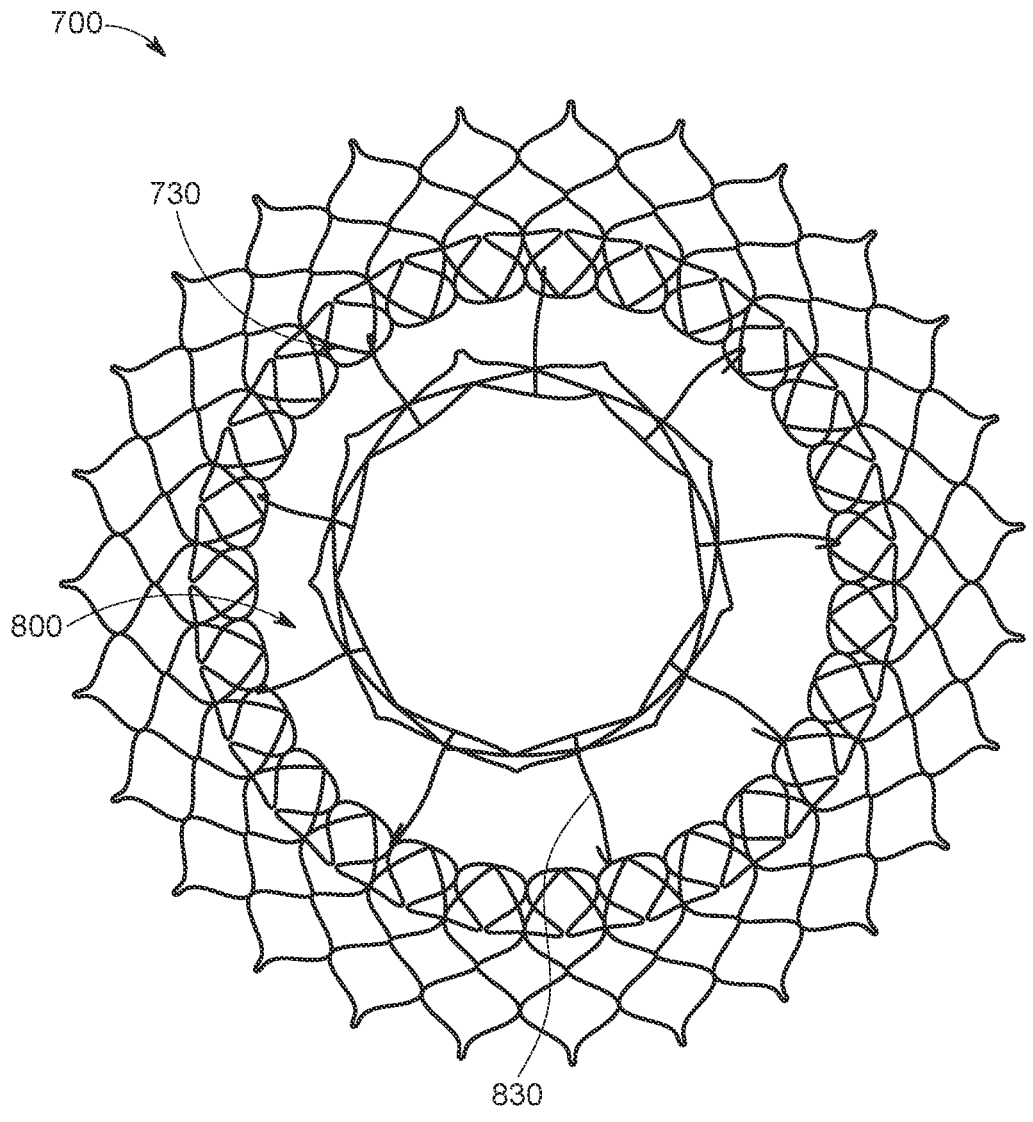
FIG. 12 is a top-down view of an outer stent coupled to an inner stent similar to that of FIG. 8.

FIG. 12 is another top-down view showing that an inner stent 800 may include more than three connectors 830. In FIG. 12, the inner stent 800 is generally similar or identical to the inner stent 500 of FIG. 8, except that a total of nine connectors 830 are provided to couple the inner stent 800 to the outer stent 700. The outer stent 700 may be generally similar to other outer stents described herein, with the main exception that there are additional connection points 730 to account for the additional connectors 830. The additional connection points 730 may be defined by or include a continuous row of cells between the atrial disc and ventricular disc. In other words, instead of having a large gap or void space between the atrial disc and ventricular disc, outer stent 700 may have complete or substantially complete circumferential rows of cells extending between the terminal ends of the outer stent.

The connectors 430, 530, 830 shown and described in connection with FIGS. 8-12 may all have a generally similar purpose. As noted earlier, the connectors 430, 530, 830 may help to mechanically isolate the generally cylindrical inner frame from the outer frame so that, even when the outer frame is distorted (for example as a result of forces applied by the native valve annulus to the outer stent during normal operation), the inner frame is able to remain substantially cylindrical, allowing the prosthetic leaflets to maintain a desirable geometry which allows for good coaptation of the bioprosthetic leaflets.

Figure 13:
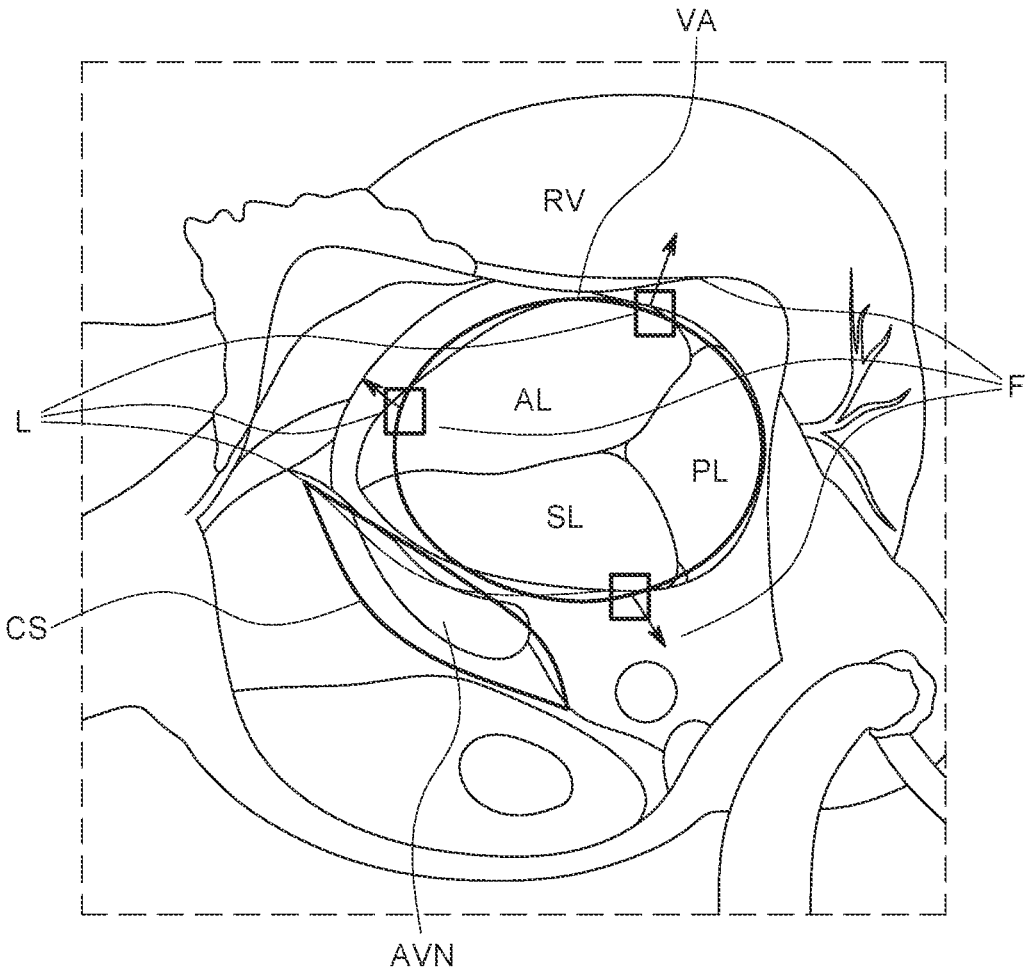
FIG. 13 is a highly schematic illustration of an outer stent similar to those of FIGS. 2-3 positioned within a native tricuspid valve.

FIG. 13 is a highly schematic representation of an outer stent similar to those of FIGS. 2-3 positioned within a native tricuspid valve. This illustration may also apply to the outer stent of FIG. 5. As shown in FIG. 13, the three posts/clips coupling the atrial disc to the ventricular disc are configured to be positioned at a clip location L, which is where the main outward forces F are applied to the valve annulus VA from the outer stent. On the other hand, the spaces devoid of metal between the posts do not provide significant force against the annulus, because there is no metal structure of the outer stent in those areas. One of those areas is preferably aligned with the conduction system CS, which includes the atrio-ventricular node AVN and/or Bundle of His (not separately labeled in FIG. 13).

Figure 14:
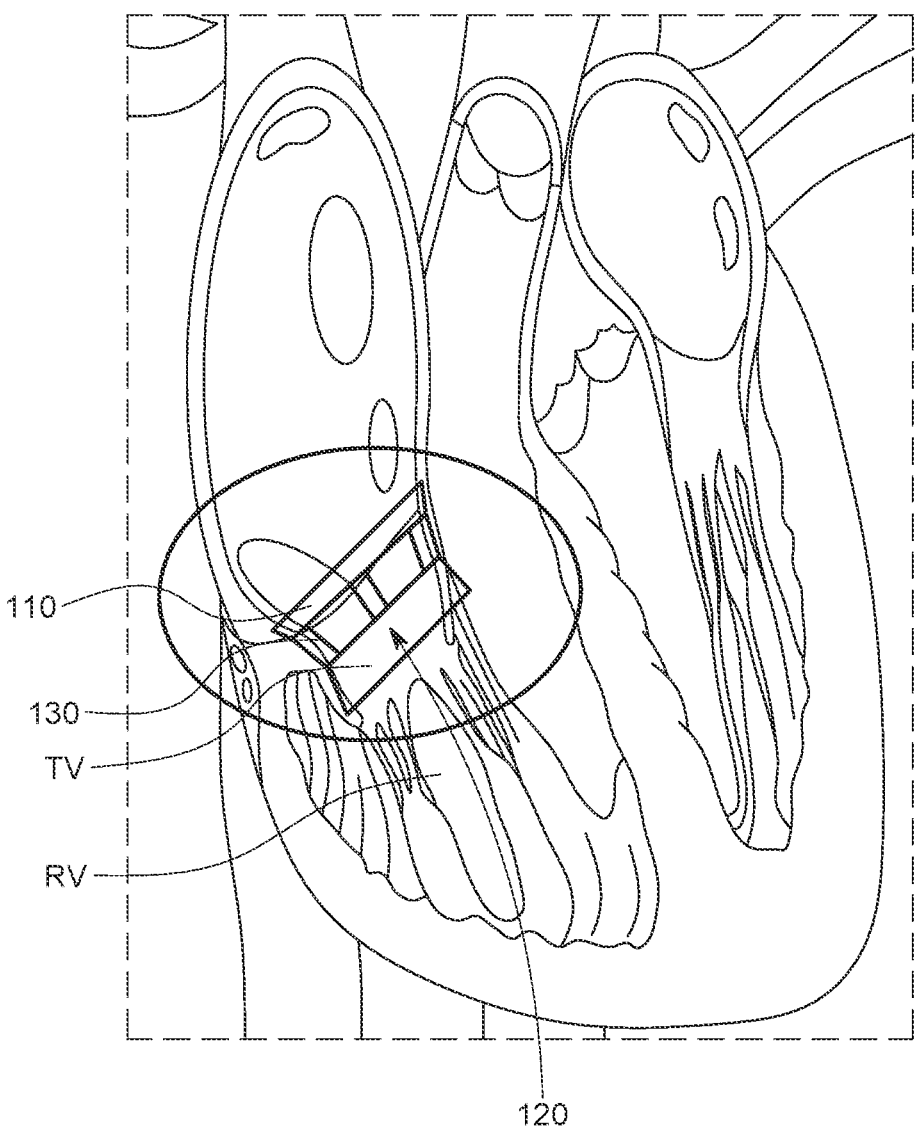
FIG. 14 is a highly schematic cross-section of the heart showing an outer stent similar to those of FIGS. 2-3 positioned within a native tricuspid valve.

FIG. 14 is a highly schematic cross-section of the heart showing an outer stent similar to those of FIGS. 2-3 positioned within a native tricuspid valve TV. This illustration may also apply to the outer stent of FIG. 5. As shown in FIG. 14, the ventricular disc 120 (or 220, 320) assist with anchoring on the ventricular side of the tricuspid valve TV, while the atrial disc 110 (or 210, 310) assists with positioning and/or anchoring on the atrial side of the tricuspid valve TV, with the posts/clips 130 (or 230, 330) spanning the two discs. For outer frames with more rows of cells in the ventricular disc than the atrial disc (such as that shown in FIG. 5), the landing zone on the ventricular side may be larger than on the atrial side.

Figure 15:
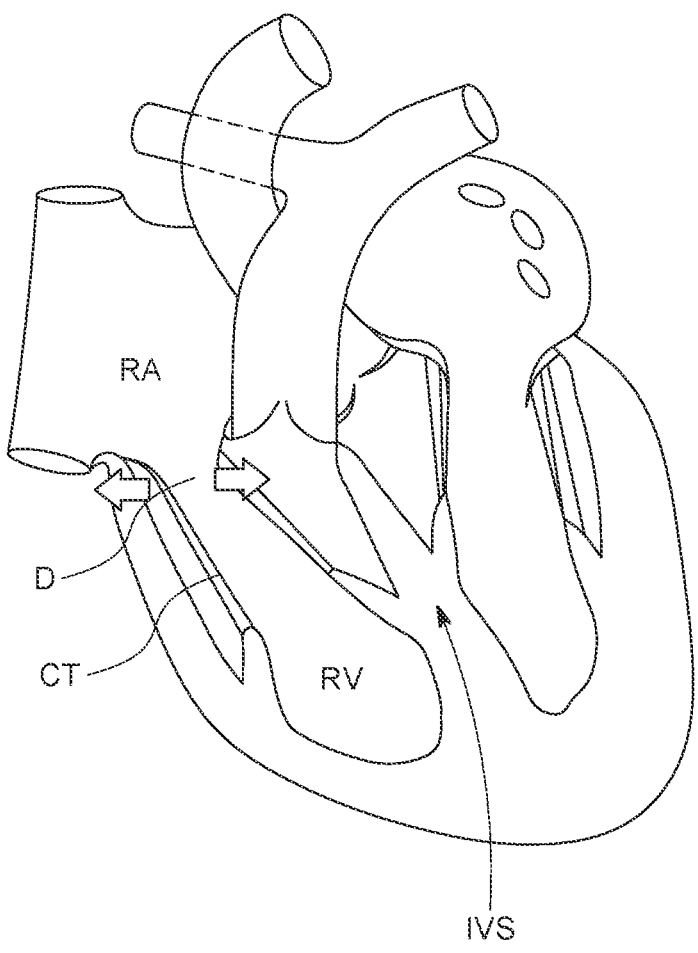
FIG. 15 is a highly schematic cross-section of the heart.

FIG. 15 is a highly schematic cross-section of the heart. As indicated in the figure, any of the outer stents described herein may include a ventricular disc section that may function, at least in part, to engage the chordae tendineae CT of the tricuspid valve (or the mitral valve), to push against the chordae tendineae CT in an outward direction D and provide enhanced anchoring within the native valve annulus.

During the process of delivering heart valve replacement and repair devices, and in particular collapsible and expandable prosthetic heart valves, it is typically useful to be able to partially or completely recapture the device after an initial partial or complete deployment of the device from a delivery catheter. For example, if the initial deployment of a prosthetic heart valve results in undesirable or suboptimal positioning of the prosthetic heart valve relative to the failing heart valve, it may be desirable to pull the prosthetic heart valve back into the delivery catheter and to either attempt a second deployment of the prosthetic heart valve to achieve a more desirable position relative to the failing heart valve, or otherwise to abort the procedure and completely remove the prosthetic heart valve from the patient. Various difficulties may be encountered when attempting to recapture an expandable prosthetic heart valve into a delivery catheter, or into a separate recapture. For example, the forces required to collapse a partially or fully expanded prosthetic heart valve to a small enough diameter to fit within a catheter may be relatively large. The forces may be even larger when the prosthetic heart valve includes a double-stent configuration, such as an any of the prosthetic heart valves described herein with an inner stent connected to an outer stent. Further, relatively flexible and relatively long intravascular delivery catheters may have more difficulty handling such recapture forces, compared to shorter and more rigid transapical catheters. Still further, recapture of a partially or fully deployed prosthetic heart valve may be more difficult when the prosthetic heart valve includes a double-flanged or hour-glass-shaped frame, compared to a frame that has a generally continuous taper from a larger diameter to a smaller diameter. Embodiments are described in greater detail below that may solve or mitigate some or all of these issues, and these solutions may be implemented for any of the prosthetic heart valves described above, as well as other specific designs of prosthetic heart valves not described above.

Figure 16:
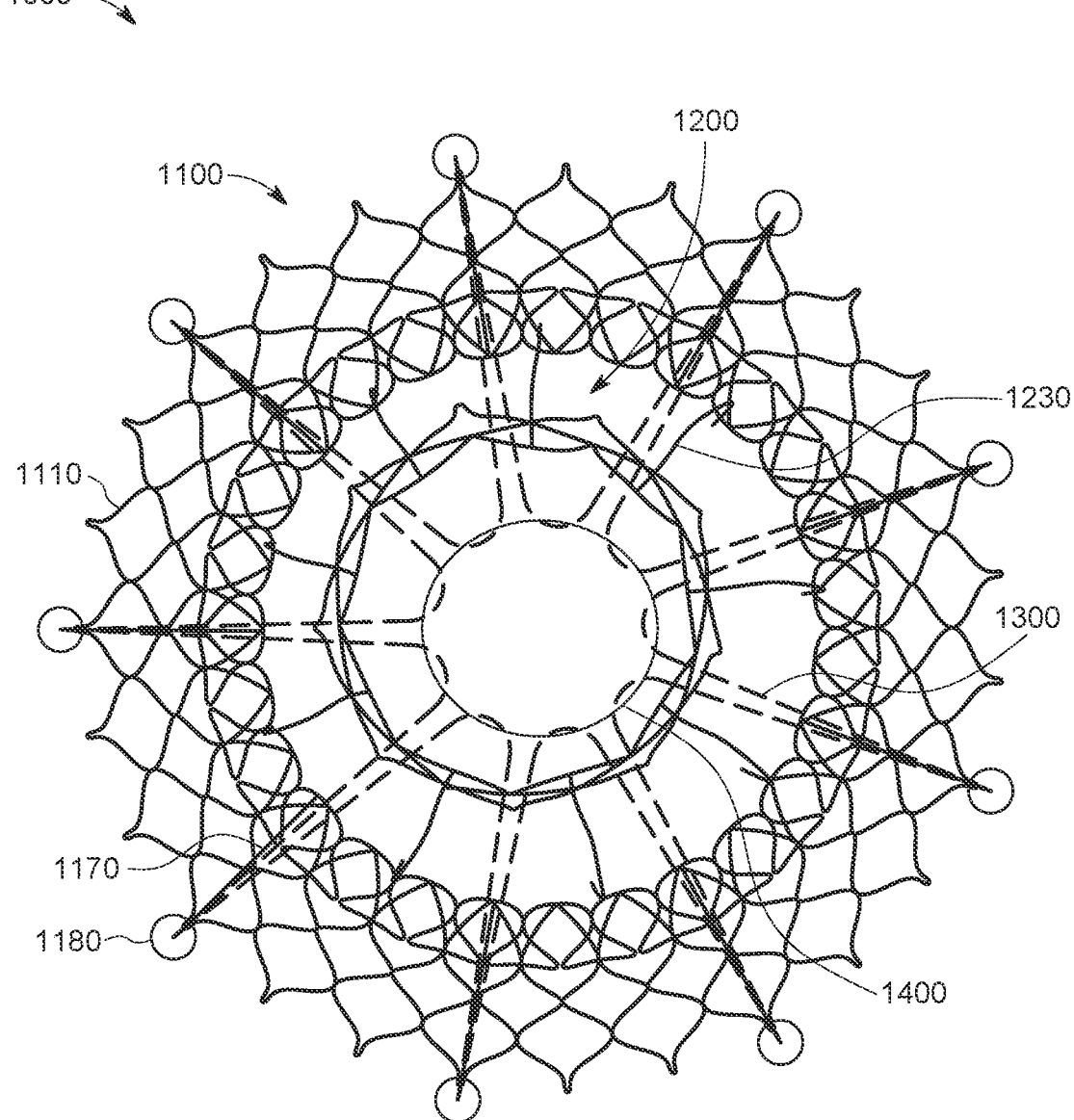
FIG. 16 is a top-down schematic view of a retrieval system coupled to a prosthetic heart valve according to an embodiment of the disclosure.
Figure 17:
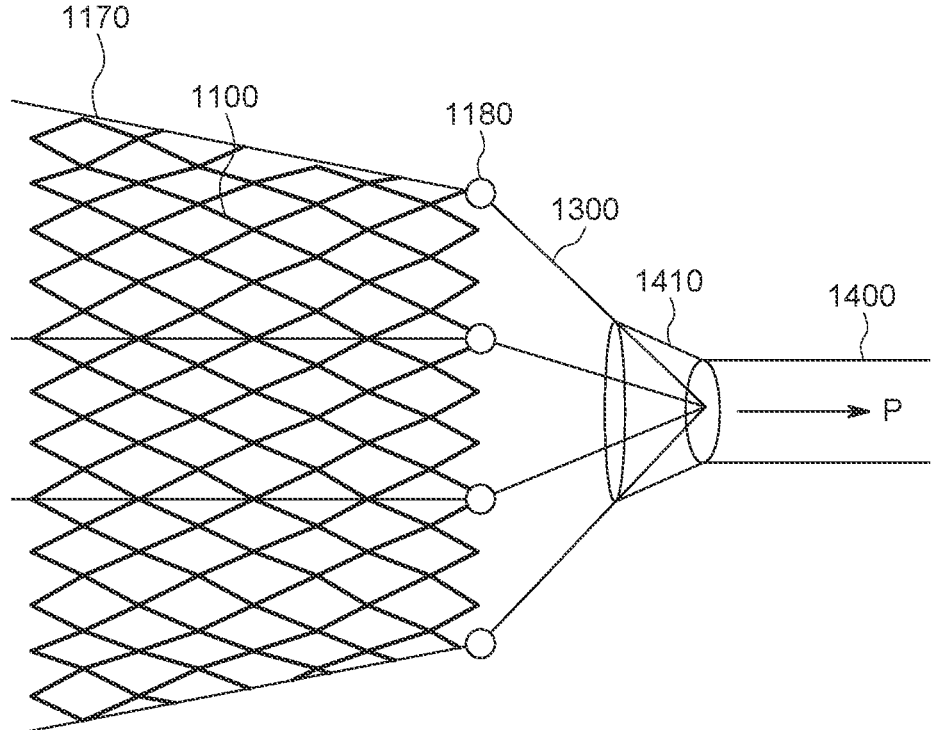
FIG. 17 is a side view of the prosthetic heart valve of FIG. 16 being re-collapsed using the retrieval system of FIG. 16.

A prosthetic heart valve 1000 is illustrated in FIGS. 16-17. Prosthetic heart valve 1000 may include an outer frame 1100 and an inner frame 1200. The inner frame 1200 may be substantially similar or identical to inner frames 500 or 800, and thus is not described in greater detail here. The outer frame 1100 may be substantially similar to outer frame 700. In other words, outer frame 1100 does not include significant gaps or voids between the atrial disc 1110 and the ventricular disc (not separately labeled), but rather outer frame 1100 defines complete or substantially complete rows of cells, which may be generally diamond-shaped cells, extending between the atrial and ventricular discs. It should be understood that, although outer frame 1100 does not include significant gaps tailored for the avoidance of conduction disturbance, the rail system described below may be applicable to various other frame designs, including designs similar or identical to outer frames 100, 200, 300, or 600. And as with other embodiments described herein, parts of the prosthetic heart valve 1000 are omitted from the figures for purposes of clarity, such as prosthetic leaflets mounted within the inner frame 1200, and sealing skirts of cuffs provided on interior and/or exterior surfaces of the outer frame 1100 and/or inner frame 1200.

As shown in FIGS. 16-17, the outer frame 1100 may include one or more rails 1170 in addition to the general diamond-shaped cell structure of the outer frame 1100. In the illustrated embodiment, a total of nine rails 1170 are illustrated, with the rails being positioned at substantially equal intervals around the circumference of the outer frame 1100. In particular, each rail 1170 is illustrated as being positioned between (in the circumferential direction) a pair of adjacent connectors 1230 of the inner frame 1200. However, the number and configuration of rails 1170 shown in FIGS. 16-17 is merely exemplary. For example, the outer frame 1100 may include more or fewer than nine rails 1170. In some embodiments, the number of rails 1170 may be equal to the number of connectors 1230, but in other examples, the number of rails 1170 may be different from the number of connectors 1230. Further, although it may be desirable for the rails 1170 to be positioned at substantially equal intervals around the circumference of the outer frame 1100, other relative positioning may be suitable. Further, although each rail 1170 is shown as being positioned at about the circumferential midpoint between a pair of adjacent connectors 1230, other relative positioning may be suitable, including radial alignment between the connectors 1230 and the rails 1170.

In some embodiments, the rails 1170 are formed of the same material as the outer frame 1100, such as a shape memory metal such as nickel-titanium alloy, including nitinol. Each rail 1170 may be formed separately from the outer frame 1100 and attached to the interior or the exterior of the outer frame via any suitable mechanism, such as fasteners (e.g., sutures) or adhesives. In other embodiments, each rail 1170 may be formed integrally with the outer frame 1100, for example via laser cutting the cells and rails 1170 of the outer frame 1100 from a single tube, such as a tube of nitinol. Whether the rails 1170 are formed separately from, or integrally with, the outer frame 1100, each rail 1170 has an axial extent that is substantially parallel to the central longitudinal axis of the prosthetic heart valve 1000. In other words, when the prosthetic heart valve 1000 is collapsed, the rails 1170 are substantially parallel to the central longitudinal axis of the prosthetic heart valve 1000. When the prosthetic heart valve is expanded, the rails 1170 may be contoured along with the inflow-to-outflow contours of the outer frame 1100, but preferably the rails 1170 do not have significant contouring in the circumferential direction of the outer frame 1100.

As shown in FIGS. 15-16, a connector 1180 may be provided at an end of each post or rail 1170. For example, each rail 1170 may include a loop or similar structure at a terminal end thereof, which may be on the side of the atrial disc 1110 which is generally collapsed first during a retrieval procedure. However, in embodiments where the ventricular disc is collapsed first during a retrieval procedure, the connectors 1180 may be positioned on the end of the rails 1170 on the side of the ventricular disc. In some embodiments, a connector 1180 may be provided on each end of the rails 1170 to allow for optionality in which end of the prosthetic heart valve 1000 is collapsed first during a retrieval procedure. Although the connectors 1180 are shown as loops or rings formed integrally with the rails 1170, in other embodiments, the connectors 1180 may take other shapes suitable for connection with control element(s) 1300, and in other embodiments the connectors 1180 may be formed on the outer stent 1100 adjacent the rails 1170.

In use, one or more control elements 1300 may be coupled to the rails 1170 via connectors 1180. For example, control elements 1300 may be flexible elements, such as wire, cords, sutures, etc. In some embodiments, a single control element 1300 may be coupled to each rail 1170. In other embodiments, a single control element 1300 may be coupled to more than one, or all, of the rails 1170, for example by looping through the connectors 1180. The control elements 1300 may extend proximally through a catheter device 1400, which may be the delivery device used for the initial deployment of the prosthetic heart valve 1000, or a separate retrieval catheter specifically designed for a retrieval and/or repositioning procedure. In some embodiments, the catheter device 1400 may include a funnel-shaped member 1410 at the end of the catheter 1400, the funnel 1410 tapering from the leading end to the trailing end where it meets the distal end of the main portion of the catheter 1400.

In one exemplary use, a delivery catheter (which may be the same as, or different than, catheter 1400) is used to deliver the prosthetic heart valve 1000 to the native tricuspid or mitral valve annulus, for example via the femoral vein, while the prosthetic heart valve 1000 is collapsed within the delivery catheter. The ventricular end of the prosthetic heart valve 1000 may be deployed first by pushing the prosthetic heart valve 1000 distally out of the delivery catheter, or by withdrawing the delivery catheter proximally relative to the prosthetic heart valve 1000. As the prosthetic heart valve 1000 exits the delivery catheter, it begins to self-expand for placement on the ventricular side of the native valve annulus. At some point after the process of deployment has begun, the operator may determine that it would be desirable to either reposition the prosthetic heart valve 1000 or remove the prosthetic heart valve 1000 from the patient entirely. If such a determination is made, the operator may pull the control element(s) 1300 in the proximal direction P relative to catheter 1400, and/or push the catheter 1400 distally relative to the control element(s) 1300. It may be more preferably to push the catheter 1400 distally while the control elements 1300 stay generally in a static position relative to the anatomy, compared to pulling the control elements 1300 proximally while the catheter 1400 stays in generally a static position relative to the anatomy, although it should be understood that either option is viable. The preference for pushing the catheter 1400 distally for retrieval may be based on the possibility that the ventricular disc is already expanded enough where pulling the ventricular disc relative to the native valve annulus may cause damage to the annulus. As noted above, this retrieval process may be performed with the original delivery catheter, or via another retrieval catheter that may be, for example, delivered over or through the original delivery catheter. This action draws the prosthetic heart valve 1000 back into the catheter 1400, forcing the expanded portions to re-collapse back into the catheter 1400. As the prosthetic heart valve 1000 is drawn into the catheter device 1400 and collapses, the rails 1170 help to distribute the re-sheathing forces, allowing the prosthetic heart valve 1000 to more easily and uniformly collapse into the catheter device 1400.

Figure 18A:
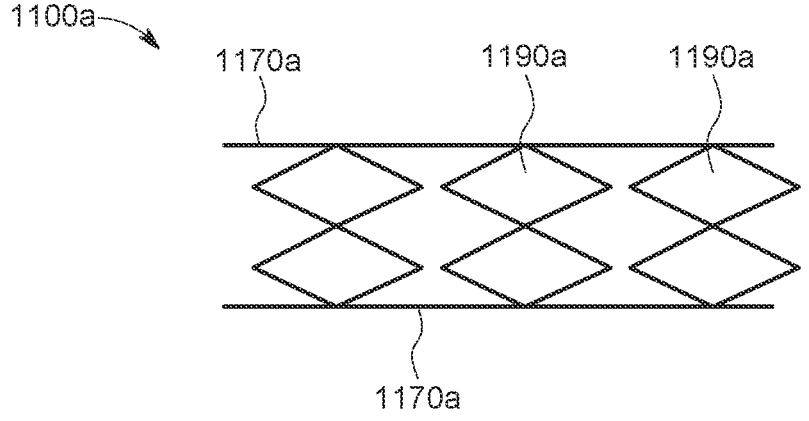
FIGS. 18A-B are schematic views of alternate constructions of a stent having rails for interaction with a retrieval system.

As noted above, in some embodiments that employ rails 1170, the rails 1170 may be formed integrally with the outer frame 1100, for example via laser cutting the cells and rails 1170 of the outer frame 1100 from a single tube, such as a tube of nitinol. FIG. 18A illustrates one exemplary mechanism of forming rails 1170a integrally with an outer frame 1100a. As shown in FIG. 18A, outer frame 1100a may include one or more rows of generally diamond-shaped cells 1190a, where each row is "free-floating" in the sense that the upper and lower apexes of one row of cells 1190a are not directly coupled to upper or lower apexes of the adjacent row or cells 1190a. Each rail 1170a couples the side apex of one cell in a row to a side apex of an adjacent cell in the same row of cells 1190a. Although FIG. 18A illustrates three rows of cells 1190a, with a rail 1170a after every second cell (e.g., two cells 1190a between each circumferentially adjacent pair of rails 1170a), it should be understood that other numbers of rows of cells 1190a may be used, and a different spacing of the rails 1170a (e.g., one cell 1190a between each circumferentially adjacent pair of rails 1170a, or three or more cells 1190a between each circumferentially adjacent pair of rails 1170a) may be suitable. Finally, it should be understood that FIG. 18A illustrates only a representative section of the outer frame 1170a.

Figure 18B:
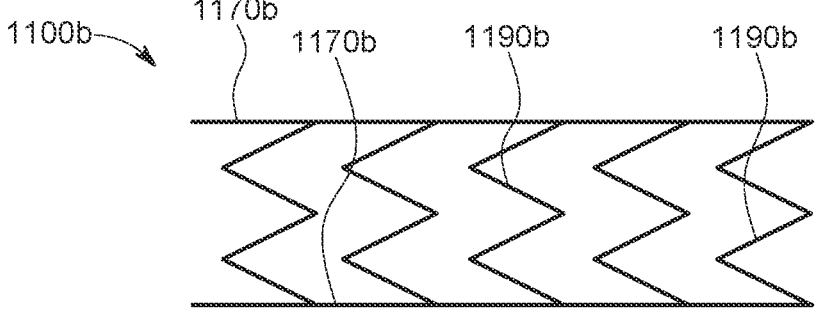

FIG. 18B illustrates a section of an outer frame 1170b which is similar in concept to outer frame 1170a, but instead of having rows of "free-floating" cells 1190a, outer frame 1170b includes rows of struts 1190b that each have a "zig-zag" pattern, with each pair of adjacent struts forming a general "V" shape with the apex of the "V" pointing in an alternating direction. Although outer frame 1100b is shown with five rows of zig-zag struts, with four struts between each pair of adjacent rails 1170b, it should be understood that the frame could include more or fewer than five rows of zig-zag struts, and each row may include more or fewer than four struts between each pair of circumferentially adjacent rails 1170b. And, although not shown, rails 1170a and 1170b may include connectors similar to those described above, including alternates described below.

As with frame 1100a, frame 1100b may be formed as an integral member—e.g., laser cut from a single tube of nitinol. The rails 1170a and 1170b do not foreshorten as the frame expands since the rails are effectively straight lines that have no capability to foreshorten. However, the "free-floating" cells 1190a may individually foreshorten upon expansion, but because adjacent rows are not directly coupled to each other, this foreshortening does not interfere with the rails 1170a. Similarly, each row of zig-zag struts 1190b may foreshorten as the frame 1100b expands, but this foreshortening does not interfere with the rails 1170b.

In the embodiments described above that include rails for retrieval and/or repositioning, it should be understood that the retrieval may be performed prior to the full release of the atrial section of the outer frame from the delivery catheter. However, in some embodiments, the retrieval may be performed after full release (e.g., complete expansion) of the prosthetic heart valve from the delivery catheter. Although it may be more difficult to retrieve the prosthetic heart valve after it has been fully released, because the required forces for retrieval would be higher than if the prosthetic heart valve has only partially expanded, it is still an option. For example, applying retrieval forces at the distal end of the catheter may assist with such retrieval. Also, while it may be generally more difficult to perform such retrieval while the delivery catheter is deflected in multiple planes, the prosthetic valve may be partially collapsed, and then moved to be positioned in the right atrium, at which the catheter may be straightened to more easily complete the retrieval.

Further, although the rails 1170 are generally shown each with a single connector 1180 at a terminal end thereof, other connector options may be suitable. For example, the rails may each include multiple connectors or eyelets along their length (e.g., at any junction where a row of "free-floating" cells 1190*a* is positioned, or where a row of zig-zag struts 1190*b* is positioned). With this embodiment, wires or sutures or other control elements may run circumferentially through eyelets of rails that are aligned so that the control elements, upon tensioning, help to force the circumferential collapse of the frame.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A collapsible and expandable prosthetic atrioventricular valve for replacing a native atrioventricular valve, the prosthetic atrioventricular valve comprising:

an outer stent having an atrial disc, a ventricular disc, and a plurality of posts coupling the atrial disc to the ventricular disc;

an inner stent including a plurality of commissure attachment features;

a plurality of connectors extending between the inner stent and the outer stent to couple the inner stent to the outer stent; and a plurality of prosthetic leaflets mounted to the plurality of commissure attachment features within the inner stent, wherein the outer stent is devoid of metal in a space circumferentially extending between adjacent ones of the plurality of posts, the space extending approximately one-third of a circumference of the outer stent, wherein, in an expanded condition of the outer stent, the ventricular disc flares radially outwardly from the plurality of posts for engaging a ventricular side of the native atrioventricular valve, the plurality of posts each have a "C"-shape or a "U"-shape facing radially outwardly for receiving portions of a native valve annulus of the native atrioventricular valve, and a diameter of the outer stent at the plurality of posts is smaller than diameters of the outer stent at the atrial disc and the ventricular disc.

2. The prosthetic atrioventricular valve of claim 1, wherein the atrial disc has two circumferential rows of cells, and the ventricular disc has one circumferential row of cells.

3. The prosthetic atrioventricular valve of claim 1, wherein the atrial disc has one circumferential row of cells, and the ventricular disc has two circumferential rows of cells.

4. The prosthetic atrioventricular valve of claim 1, wherein the plurality of posts includes three posts, each of the three posts including two struts extending from the atrial disc to the ventricular disc.

5. The prosthetic atrioventricular valve of claim 4, wherein the two struts of each of the three posts has a first end coupled to a respective first apex of a cell in the atrial disc, and a second end coupled to a respective second apex of a cell in the ventricular disc.

6. The prosthetic atrioventricular valve of claim 5, wherein each of the three posts includes a tine between the two struts.

7. The prosthetic atrioventricular valve of claim 6, further comprising an aperture formed in one of the two struts or the tine of each of the three posts, each of the plurality of connectors being coupled to the outer stent via a corresponding one of the apertures.

8. The prosthetic atrioventricular valve of claim 1, wherein the inner stent includes a circumferential row of first cells having a total number, and the outer stent includes a circumferential row of second cells having a total number, the total number of second cells being a whole number multiple of the total number of first cells.

9. The prosthetic atrioventricular valve of claim 8, wherein the total number of second cells is twenty-seven, and the total number of first cells is nine.

10. A method of replacing a native atrioventricular valve of a heart, the method comprising:

delivering a prosthetic atrioventricular valve to the native atrioventricular valve while the prosthetic atrioventricular valve is collapsed within a delivery catheter, the prosthetic atrioventricular valve including an outer stent, an inner stent having a plurality of commissure attachment features and being coupled to the outer stent, and a plurality of prosthetic leaflets mounted to the plurality of commissure attachment features within the inner stent; a plurality of connectors extending between the inner stent and the outer stent to couple the inner stent to the outer stent; and deploying the prosthetic atrioventricular valve from the delivery catheter to allow the prosthetic atrioventricular valve to self-expand;

wherein allowing the prosthetic atrioventricular valve to self-expand includes positioning an atrial disc of the outer stent on an atrial side of the native atrioventricular valve and positioning a ventricular disc of the outer stent on a ventricular side of the native atrioventricular valve;

wherein after the prosthetic atrioventricular valve has self-expanded into the native atrioventricular valve, a gap in the outer stent between an adjacent pair of posts of a plurality of posts that connect that atrial disc to the ventricular disc is aligned with a conduction system of the heart, the outer stent being devoid of metal in a space circumferentially extending between adjacent ones of the plurality of posts, the space extending approximately one-third of a circumference of the outer stent; and wherein after the prosthetic atrioventricular valve has self-expanded into the native atrioventricular valve, the ventricular disc flares radially outwardly from the plurality of posts to engage the ventricular side of the native atrioventricular valve, the plurality of posts each have a "C"-shape or a "U"-shape facing radially outwardly for receiving portions of a native valve annulus of the native atrioventricular valve, and a diameter of the outer stent at the plurality of posts is smaller than diameters of the outer stent at the atrial disc and the ventricular disc.

* * * * *